United States Patent [19]

Zondler et al.

[11] Patent Number: 4,959,096
[45] Date of Patent: Sep. 25, 1990

[54] COMPOSITIONS FOR PROTECTING PLANTS AGAINST DISEASE

[75] Inventors: Helmut Zondler, Bottmingen; Walter Kunz, Oberwil, both of Switzerland

[73] Assignee: Ciba-Geigy Corporation, Ardsley, N.Y.

[21] Appl. No.: 324,876

[22] Filed: Mar. 17, 1989

[30] Foreign Application Priority Data

Mar. 25, 1988 [CH] Switzerland ............ 1140/88

[51] Int. Cl.$^5$ .................. A61K 31/455; C07D 211/86
[52] U.S. Cl. ..................... 514/356; 514/355; 514/340; 514/341; 514/336; 514/332; 546/322; 546/315; 546/263; 546/283; 546/284; 546/278; 546/276
[58] Field of Search ............... 546/322, 315, 263, 283, 546/284, 278, 276; 514/356, 355, 340, 341, 336, 332

[56] References Cited

U.S. PATENT DOCUMENTS 4,137,067 1/1979 Gätzi ........................ 71/94

FOREIGN PATENT DOCUMENTS 1072443 2/1980 Canada .
384929 2/1965 Switzerland .
923387 4/1963 United Kingdom .

OTHER PUBLICATIONS

CA 110: 110110h, 1989, JP 6393766.
Chem. Abstract, 57: 4769a (1962), Abstract of Acta Fa. Pharm. Brun. Bratislar., 4, 65,66 (1962).

Primary Examiner—Jane T. Fan
Attorney, Agent, or Firm—Edward McC. Roberts; George R. Dohmann

[57] ABSTRACT

Novel substituted isonicotinic acid esters of the general formula

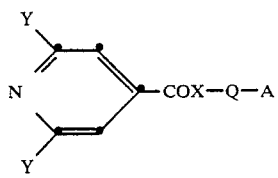

in which
Y is halogen;
X is oxygen or sulfur;
Q is $C_1$–$C_3$alkylene, propenylene, $C_1$–$C_3$alkylene mono- or di-substituted by R, or propenylene mono- or di-substituted by R;
R is $C_1$–$C_4$alkyl, $C_1$–$C_4$haloalkyl having from 1 to 3 halogen atoms, cyano, $C_2$–$C_5$alkoxycarbonyl, $C_3$–$C_6$-cycloalkyl, phenyl, or phenyl substituted by $C_1$–$C_4$alkyl, $C_1$–$C_4$alkoxy, halogen, trifluoromethyl, tricholoromethyl, nitro or by cyano, or benzoyl or benzoyl substituted by $C_1$–$C_4$alkyl, $C_1$–$C_4$alkoxy, trifluoromethyl, trichloromethyl, nitro or by cyano;
A is phenyl, biphenyl, phenoxyphenyl, naphthyl, pyridyl, furyl, thienyl, imidazolyl or triazolyl, it being possible for each of these radicals to be unsubstituted or substituted by halogen, $C_1$–$C_4$alkyl, $C_1$–$C_3$alkoxy, $C_1$–$C_3$haloalkoxy having from 1 to 3 halogen atoms, trifluoromethyl, nitro or by cyano; with the proviso (1) that if A is imidazolyl or triazolyl R may not be phenyl or benzoyl, and (2) that A and the R substituent in Q may together contain no more than 3 rings.

The novel active ingredients have plant-protecting properties and are suitable especially for the preventive protection of plants against attack by phytopathogenic microorganisms, such as fungi, bacteria and viruses.

8 Claims, No Drawings

COMPOSITIONS FOR PROTECTING PLANTS AGAINST DISEASE

The present invention relates to novel substituted isonicotinic acid esters of the following formula I. The invention relates also to the preparation of those substances and to compositions containing at least one of those compounds as active ingredient. The invention furthermore relates to the preparation of the said compositions and to the use of the active ingredients or compositions for protecting plants against attack by harmful microorganisms, for example plant-damaging fungi, bacteria and viruses.

The compounds of the invention correspond to the general formula I

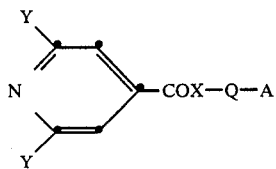

in which
Y is halogen;
X is oxygen or sulfur;
Q is $C_1$–$C_3$alkylene, propenylene, $C_1$–$C_3$alkylene mono- or di-substituted by R, or propenylene mono- or di-substituted R;
R is $C_1$–$C_4$alkyl, $C_1$–$C_4$haloalkyl having from 1 to 3 halogen atoms, cyano, $C_2$–$C_5$alkoxycarbonyl, $C_3$–$C_6$cycloalkyl, phenyl, or phenyl substituted by $C_1$–$C_4$alkyl, $C_1$–$C_4$alkoxy, halogen, trifluoromethyl, trichloromethyl, nitro or by cyano, or benzoyl or benzoyl substituted by $C_1$–$C_4$alkyl, $C_1$–$C_4$alkoxy, trifluoromethyl, trichloromethyl, nitro or by cyano;
A is phenyl, biphenyl, phenoxyphenyl, naphthyl, pyridyl, furyl, thienyl, imidazolyl or triazolyl, it being possible for each of these radicals to be unsubstituted or substituted by halogen, $C_1$–$C_4$alkyl, $C_1$–$C_3$alkoxy, $C_1$–$C_3$haloalkoxy having from 1 to 3 halogen atoms, trifluoromethyl, nitro or by cyano; with the proviso (1) that if A is imidazolyl or triazolyl R may not be phenyl or benzoyl, and (2) that A and the R substituent in Q may together contain no more than 3 rings.

Halogen on its own or as a component of another substituent is fluorine, chlorine, bromine or iodine, preferably chlorine or bromine, and more especially chlorine.

Alkyl on its own or as a component of another substituent is to be understood as meaning straight-chain or branched alkyl. Depending on the number of carbon atoms indicated it represents, for example, one of the following groups: methyl, ethyl and the isomers of propyl or butyl, such as, for example, isopropyl, isobutyl, tert.-butyl or sec.-butyl.

The invention relates especially to compounds of formula I in which
Y is halogen;
X is oxygen or sulfur;
Q is $C_1$–$C_3$alkylene, propenylene, $C_1$–$C_3$alkylene mono- or di-substituted by R, or propenylene mono- or di-substituted by R;
R is $C_1$–$C_4$alkyl, $C_1$–$C_4$haloalkyl having from 1 to 3 halogen atoms, cyano, $C_2$–$C_5$alkoxycarbonyl, $C_3$–$C_6$cycloalkyl, phenyl, or phenyl substituted by $C_1$–$C_4$alkyl, $C_1$–$C_4$alkoxy, trifluoromethyl, trichloromethyl, nitro or by cyano, or benzoyl or benzoyl substituted by $C_1$–$C_4$alkyl, $C_1$–$C_4$alkoxy, trifluoromethyl, trichloromethyl, nitro or by cyano;
A is phenyl, biphenyl, phenoxyphenyl, naphthyl, pyridyl, furyl, thienyl, imidazolyl or triazolyl, it being possible for each of these radicals to be unsubstituted or substituted by halogen, $C_1$–$C_4$alkyl, $C_1$–$C_3$alkoxy, trifluoromethyl, nitro or by cyano; with the proviso (1) that if A is imidazolyl or triazolyl R may not be phenyl or benzoyl, and (2) that A and the R substituent in Q may together contain no more than 3 rings.

The cyclic radicals defined as substituted for formula I are preferably mono- to tri-substituted The compounds of formula I can be divided into the following groups on the basis of their special plant-protecting properties:

1. Compounds of formula I in which
Y is simultaneously chlorine or bromine;
X is oxygen;
Q is methylene or methylene substituted by R;
R is $C_1$–$C_3$alkyl, phenyl or phenyl substituted by halogen or by methoxy;
A is phenyl, phenyl substituted by halogen, or pyridyl, furyl, thienyl, imidazolyl or triazolyl.

2. Compounds of formula I in which
Y is chlorine;
X is oxygen;
Q is methylene substituted by R;
R is methyl, ethyl, phenyl or 2,4-dichlorophenyl;
A is phenyl substituted by chlorine and/or by fluorine, especially 2,4-dichlorophenyl.

The following compounds are distinguished by especially advantageous plant-protecting properties:
2,6-dichloroisonicotinic acid benzyl ester;
2,6-dichloroisonicotinic acid α-methylbenzyl ester;
2,6-dichloroisonicotinic acid α-ethylbenzyl ester;
2,6-dichloroisonicotinic acid α-phenylbenzyl ester;
2,6-dichloroisonicotinic acid α-(4-chlorophenyl)-benzyl ester.

Some 2,6-dihaloisonicotinic acid derivatives are already known. For example, 2,6-dihaloisonicotinic acid derivatives, for example the free acids and some of their esters and salts, are described as herbicides in Swiss Patent Specification No. 384 929 and British Patent Specification No. 923 387. Furthermore, U.S. Pat. No. 4,137,067 and Canadian Patent Specification No. 1 072 443 disclose 2,6-dichloroisonicotinic acid alkyl esters as intermediates for the preparation of hydrazide derivatives, described as fungicidally active, of the aforementioned isonicotinic acid compounds. In addition, 2,6-dihaloisonicotinic acid derivatives are known as tuberculostatic agents (cf. Acta Fac. Pharm. Brun. Bratislav. 4, 65–66 [1962]; Chem. Abst. Vol. 57, 1962, 4769b).

It has now surprisingly been found that the use of compounds of formula I of the invention prevents plants from being attacked by harmful microorganisms and thus guards against damage to plants caused by such attack. A characteristic of the active ingredients of the invention is that the protection of the plants can stem both from the direct action on the plant-damaging microorganisms by means of foliar application (direct action) or soil application (systemic action) and from the activation and stimulation of the plant's own defence system (immunisation). The great advantage of the compounds of formula I is that it is possible to ensure the continued health of plants treated with these substances also through their own resources, without using further microbicidal substances during the vegetation period. Consequently it is possible by using the active ingredients of the invention to avoid the adverse side effects that may occur, for example, with direct parasite control using chemical substances, for example on the one hand as a result of damage to the useful plants (phytotoxicity) and on the other hand as a result of causing the harmful microorganisms to develop a resistance; consequently growth of the useful plants is advantageously completely undisturbed.

Owing to the double action of the compounds of formula I of the invention, that is to say on the one hand the direct control of the plant pathogens and on the other hand the increase in the general capacity of plants treated with these active ingredients to defend themselves as a result of immunisation, it is possible to achieve a broadly based protection of plants against disease. The use of the active ingredients of the invention is therefore especially suitable for practical application. Furthermore, the systemic activity peculiar to the compounds of formula I results in the protective effect being extended also to growing parts of the treated plants.

The general plant-protecting activity of the active ingredients of the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example of the genera Hemileia, Rhizoctonia, Puccinia); Ascomycetes (for example Venturia, Podosphaera, Erysiphe, Monilinia, Uncinula).

In addition, the active ingredients can be used with particular advantage against the following harmful organisms: fungi, such as, for example, Oomycetes (for example *Plasmopara viticola, Phytophthora infestans, Peronospora tabacina,* Pseudoperonospora), Fungi imperfecti (for example *Colletotrichum lagenarium, Piricularia oryzae, Cercospora nicotinae*), Ascomycetes (for example *Venturia inaequalis*); bacteria, such as, for example, Pseudomonads (*Pseudomonas lachrymans, Pseudomonas tomato, Pseudomonas tabaci*); Xanthomonads (for example *Xanthomonas oryzae, Xanthomonas vesicatoria*); Erwinia (for example *Erwinia amylovora*); and viruses, such as, for example, the Tobacco Mosaic Virus.

The compounds of the invention can be used to protect plants of various useful crops.

The following species of plants, for example, are suitable for the use within the scope of the invention of compounds of formula I of the invention: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (pumpkin, cucumber, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The following plants are to be regarded as especially suitable target crops for the application of the process of the invention: cucumber, tobacco, vines, rice, pepper, potatoes, tomatoes, wheat, barley, pears and apples.

The compounds of formula I are obtained from 2,6-dihaloisonicotinic acid halides, anhydrides or azolides.

The compounds of formula I are prepared by reacting:

(a) an isonicotinic acid halide of formula II

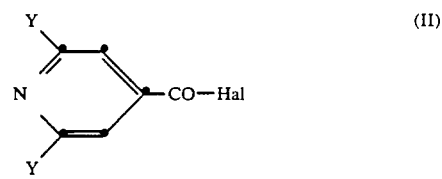

or (b) an isonicotinic acid anhydride of formula IV

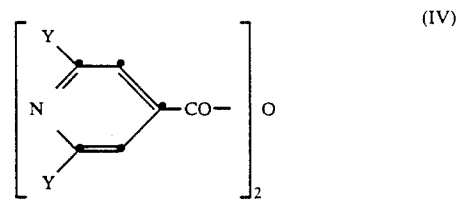

or (c) an isonicotinic acid azolide of formula V

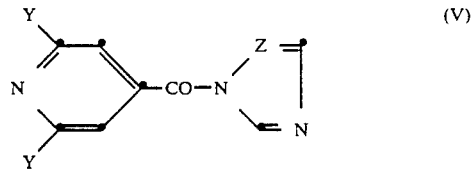

or (d) an isonicotinic acid derivative of formula VI

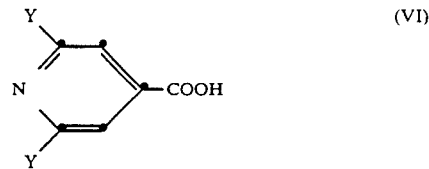

with an alcohol of formula III

wherein Z is CH or N and Y, A, Q and X are as defined for formula I.

The reactions are advantageously carried out in the presence of an inert solvent.

Reaction variants (a) and (b) are carried out in the presence of a base.

Suitable reaction temperatures for reaction variants (a), (b) and (c) are from $-20°$ to $150°$ C., preferably from $0°$ to $80°$ C., and for reaction (d) from $0°$ to $180°$ C., preferably from $10°$ to $110°$ C.

A catalyst is required for reaction variant (d). Suitable catalysts are Lewis acids, such as, for example, boron trifluoride diethyl etherate, or mineral acids, such as, for example, sulfuric acid, HCl or HBr (gaseous), but also bases, such as, for example, tertiary amines, pyridines or alkaline alcoholates. Further examples of suitable catalysts are familiar to the skilled person.

Suitable bases for binding the acid in process variants (a) and (b) are organic and inorganic bases, for example tertiary amines, such as trialkylamines (trimethylamine, triethylamine, tripropylamine etc.), pyridine, pyridine bases (4-dimethylaminopyridine, 4-pyrrolidylaminopyridine etc.) and oxides and hydroxides, carbonates and hydrogen carbonates of alkali metals and alkaline earth metals, and also alkali metal acetates.

Suitable solvents and diluents that are inert towards the reactions are used as reaction media in process variants (a) and (b) in accordance with the respective reaction conditions. The following may be mentioned as examples: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.) anisole, dioxan, tetrahydrofuran; nitriles, such as acetonitrile, propionitrile; N,N-dialkylated amides, such as dimethylformamide; dimethyl sulfoxide; ketones, such as acetone, diethyl ketone, methyl ethyl ketone; and also mixtures of such solvents with one another.

Reactions analogous to process variants (a) to (d) are described in the literature, for example in Acta. Fac. Pharm. Bohemoslovenica IV, 1962, 65.

The starting materials for the preparation of compounds of formula I are known or can be prepared according to known methods. For example, the preparation of alcohols of formula III is described, for example, in Houben-Weyl, Vol. 6/1a/1b and Vol. 9.

The preparation of the compounds of formula V

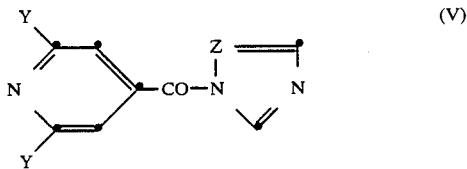

(V)

used as starting materials is carried out by reacting a compound of formula II

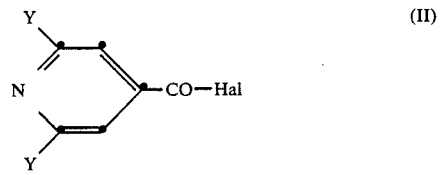

(II)

with an azole of formula VI

(VI)

in an inert solvent in the presence of a base, Y having the meanings given for formula I, Hal being halogen, preferably chlorine, and Z being an N-atom or CH.

The reaction temperatures for the above-described synthesis are from −50° to 200° C., preferably from 10° to 100° C.

Suitable bases and solvents are those mentioned for the preparation of compounds of formula I.

Reactions of acid halides with azoles are described in Angew. Chemie 1962, p. 409–411.

The starting materials of formula V

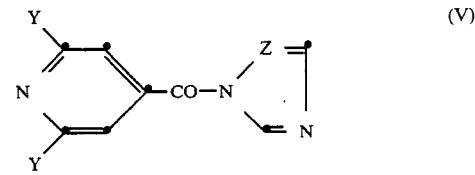

(V)

in which Y is simultaneously fluorine, chlorine, bromine or iodine and Z is either N or CH, are valuable intermediates for the preparation of the compounds of formula I of the invention. The compounds of formula V are novel substances that also have a protecting activity against the mentioned phytopathogens. The present invention relates also to those compounds.

The compositions that are used within the scope of the invention for protecting plants against disease and that contain the compounds of formula I as active ingredients are to be considered as part of the invention.

The compounds of formula I are normally used in the form of compositions and can be applied to the plant or crop area to be treated, simultaneously or in succession, with further compounds. These further compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

One method of applying a compound of formula I or an agrochemical composition containing at least one of those compounds is application to the plant (foliar application). The compounds of formula I can, however, also penetrate the plant through the roots via the soil (soil application) if the locus of the plant is impregnated with a liquid formulation, or if the compounds are applied in solid form to the soil, for example in granular form. The compounds of formula I may, however, also be applied to seeds (coating), either by impregnating the seeds with a liquid formulation of the compound, or coating them with a solid formulation (dressing). In addition, in special cases further types of application are possible, for example the selective treatment of the plant stems or buds.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are especially quaternary ammonium salts that contain as N-substituent at least one alkyl radical having from 8 to 22 carbon atoms and as further substituents lower, unsubstituted or halogenated alkyl, benzyl or hydroxy-lower alkyl radicals.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil.

Suitable synthetic surfactants are especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts or unsubstituted or substituted ammonium salts and contain an alkyl radical having from 8 to 22 carbon atoms.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries, such as stabilisers, antifoams, viscosity regulators, binders, tackifiers as well as fertilisers or other active ingredients for achieving special effects.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

The following Examples serve to illustrate the invention without implying any limitation.

1. PREPARATION EXAMPLES

EXAMPLE 1.1

Preparation of 1,2,4-triazol-1'yl-methoxycarbonyl-4'yl-(2,6-dichloropyridine)

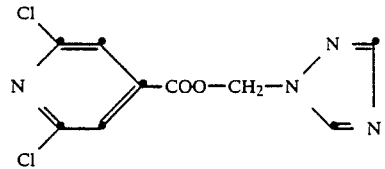

7.8 g of 2,6-dichloroisonicotinic acid chloride are added dropwise to 3.3 g of hydroxymethyl-1,2,4-triazol-1'yl in 50 ml of absolute pyridine while cooling with ice at 0°–15°. The batch is then stirred at room temperature for 4 hours, cooled and partitioned between water and dichloromethane. The organic extract is washed with water, dried and concentrated by evaporation. Drying under a high vacuum and subsequent recrystallisation from tetrahydrofuran/ligroin yields 5.3 g of the title compound with a melting point of 78°–80° C.

EXAMPLE 1.2

Preparation of 2,6-dichloroisonicotinic acid benzyl ester

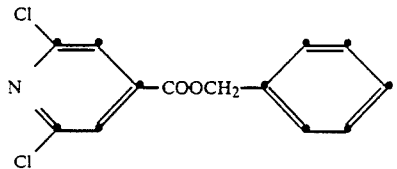

7.8 g of 2,6-dichloroisonicotinic acid chloride, dissolved in 10 ml of acetonitrile, are added dropwise to a solution, maintained at 15°–20° C. by cooling, of 5.4 g of benzyl alcohol, 0.5 g of 4-dimethylaminopyridine and 3.0 g of pyridine in 50 ml of acetonitrile. After stirring overnight at room temperature the batch is poured onto ice-water, taken up in methylene chloride, washed with water, dried and concentrated by evaporation. The oil that remains crystallises from pentane in the form of white crystals having a melting point of 39°–41° C.

EXAMPLE 1.3

2,6-dichloroisonicotinic acid ?-(4-chlorophenyl)-benzyl ester

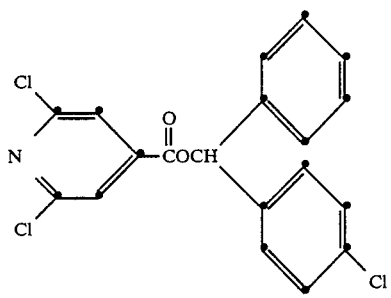

3.28 g (0.015 mole) of α-(4-chlorophenyl)-benzyl alcohol are dissolved in 30 ml of tetrahydrofuran with 0.5 ml of triethylamine. After the addition of 4.12 g (0.017 mole) of 2,6-dichloroisonicotinoylimidazole, the batch is stirred at room temperature. Within a period of 30 minutes the suspension turns into a solution. The reaction is complete after 3.5 hours. Only traces of the alcohol used can at that point be detected by thin-layer chromatography. The solution is extracted with water and ethyl acetate and the organic phase is dried over sodium sulfate to yield, after removal of the solvent in a rotary evaporator, 6.1 g of oil. This is chromatographed over silica gel with a mixture of 4 parts hexane and 1 part ethyl acetate. Removal of the solvent from the pure fractions yields 5.45 g in the form of a colourless viscous resin.

$^1$H-NMR (CDCl$_3$; ppm values): 7.1 (>CHO—); 7.3–7.4 (9 arom. H); 7.8 (2H; pyridine ring).

EXAMPLE 1.4

Preparation of the precursor to Example 1.3
α-(4-chlorophenyl)-benzyl alcohol

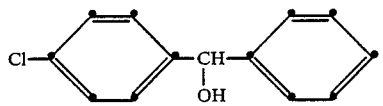

15.2 g (0.07 mole) of phenyl-(4-chlorophenyl)-ketone are dissolved in 30 ml of tetrahydrofuran and 10 ml of methanol. 1.32 g (0.035 mole) of sodium borohydride are gradually added, with stirring, and the exothermic reaction is maintained between 25° and 30° C. by cooling. After one hour ketone can no longer be detected by thin layer chromatography. The mixture is then extracted with water and chloroform, the chloroform is dried with sodium sulfate and removed in a rotary evaporator. The crude yield is 16.2 g (oil). Of this 15.5 g are distilled at 220° C. and 30 mbar in a bulb tube oven. 14.3 g of an oil are obtained which is more than 95% pure according to gas chromatography and solidifies into crystals on cooling. 13.3 g are recrystallised from a mixture of 25 ml of n-hexane and 5 ml of cyclohexane. The yield is 12.2 g; m.p. 58°–60° C.

The compounds listed in the following are obtained in accordance with the methods of preparation described above.

Radicals A$_2$ to A$_{10}$ in the Tables (for example Table 3) have the following meanings:

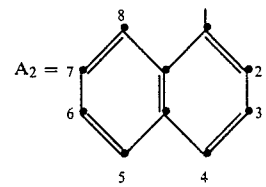

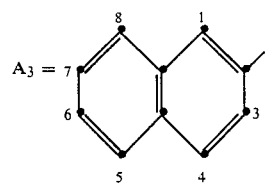

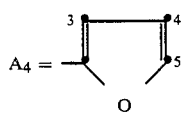

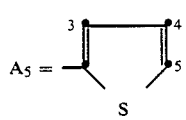

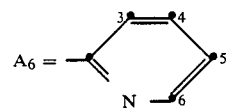

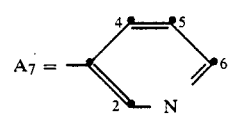

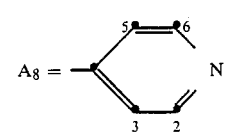

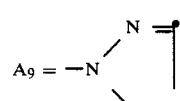

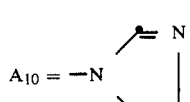

TABLE 1

[Structure: 3,5-dichloropyridine-2-carboxylic acid ester with -COO-Q'-phenyl-A']

| No. | Q' | A' | physical data |
|---|---|---|---|
| 1.1 | —CH₂ | H | m.p. 39–41° |
| 1.2 | —CH(CH₃)— | H | |
| 1.3 | —CH(C₂H₅)— | H | |
| 1.4 | —CH(-cyclopropyl)— | H | |
| 1.5 | —CH(CH₃)— | 2,4-di-Cl | $n_D^{50}$ 1,5731 |
| 1.6 | —CH(C₂H₅)— | 2,4-di-Cl | $n_D^{50}$ 1,5683 |
| 1.7 | —CH(phenyl)- | 4-Cl | resin |
| 1.8 | —CH(4-chlorophenyl)- | 3,4-di-OCH₃ | $n_D^{50}$ 1,5939 |
| 1.9 | —CH₂— | 2-Cl | |
| 1.10 | —CH₂— | 3-Cl | |
| 1.11 | —CH₂— | 4-CH₃ | |
| 1.12 | —CH₂— | 4-NO₂ | |
| 1.13 | —CH(C₂H₅)— | 4-OCH₃ | $n_D^{30}$ 1,5604 |
| 1.14 | —CH(C₂H₅)— | H | |
| 1.15 | —CH(C₂H₅)— | 4-Cl | |
| 1.16 | —CH₂ | 3-F | |
| 1.17 | —CH₂— | 4-CF₃ | m.p. 81–83° C. |
| 1.18 | —CH₂— | 2-F | |
| 1.19 | —CH₂— | 4-F | |
| 1.20 | —CH₂—CH₂— | H | |
| 1.21 | —CH₂— | 2-NO₂ | |
| 1.22 | —CH₂— | 2-CH₃ | |
| 1.23 | —CH₂— | 4-C₆H₅ | |
| 1.24 | —CH₂— | 4-O—C₆H₅ | |
| 1.25 | —C(phenyl)₂- | H | |
| 1.26 | —CH(COOCH₃)— | H | $n_D^{30}$ 1,5593 |
| 1.27 | —CH(COOC₂H₅)— | H | |
| 1.28 | —CH(COOC₃H₇(i)) | H | |
| 1.29 | —CH(COOC₄H₉(n) | H | |
| 1.30 | —CH(COOCH₃)— | 2,4-di-Cl | |
| 1.31 | —CH(COOCH₃)— | 2-Cl | |
| 1.32 | —CH(COOCH₃)— | 3-Cl | |
| 1.33 | —CH(COOCH₃)— | 4-Cl | |
| 1.34 | —CH(COOCH₃)— | 2-F | |
| 1.35 | —CH₂— | 3-CN | |
| 1.36 | —C(CH₃)COOCH₃ | H | |
| 1.37 | —CH₂—CH=CH— | H | $n_D^{30}$ 1,5973 |
| 1.38 | —CH₂—CH₂—CH₂— | 3,4-di-OCH₃ | |
| 1.39 | —C(CH₃)₂ | H | |
| 1.40 | —CH(4-chlorophenyl)- | 2,4-di-OCH₃ | |
| 1.41 | —CH(C₆H₅)— | H | oil |
| 1.42 | —CH(CH₃)— | 4-Br | |
| 1.43 | —CH(C₆H₅)— | 4-Br | |
| 1.44 | —CH(C₆H₅)— | 4-Cl | |
| 1.45 | —CH(CH₃)— | 4-C₆H₅ | |
| 1.46 | —CH(4-methoxyphenyl)- | 4-OCH₃ | |
| 1.47 | —CH(C₆H₅)CH₂CH₂— | H | |
| 1.48 | —CH(CH₃)CH₂CH₂— | H | |
| 1.49 | —CHCOC₆H₅ | H | m.p. 165–167° C. |
| 1.50 | —CH(CH₃)— | 2,4,6-trimethyl | |
| 1.51 | —CH(CH₂)₂CH₃— | H | |
| 1.52 | —CH(CH₃)— | 2-Cl | |
| 1.53 | —CH(CH₃)— | 4-Cl | |
| 1.54 | —CH(CH₃)— | 3,4-di-OCH₃ | $n_D^{30}$ 1,5634 |
| 1.55 | —CH₂— | 2,4-di-F | |
| 1.56 | —CH(CH₃)— | 2,4-dimethyl | |
| 1.57 | —CH(CH₃)— | 2-F | |
| 1.58 | —CH(CH₃)— | 4-F | |
| 1.59 | —CH(CH(CH₃)₂)— | H | |
| 1.60 | —CH(CH₃)— | 2-OCH₃ | |
| 1.61 | —CH(CH₃)— | 3-OCH₃ | |
| 1.62 | —CH(CH₃)— | 4-OCH₃ | m.p. 46–48° C. |
| 1.63 | —CH(4-CH₃OC₆H₄)— | H | |
| 1.64 | CH(C₃H₇(n))— | 4-OCH₃ | |
| 1.65 | —CH(CH₃)— | O—CH₃ | |
| 1.66 | —CH(CH₃)— | 3-CH₃ | $n_D^{30}$ 1,5594 |

TABLE 1-continued

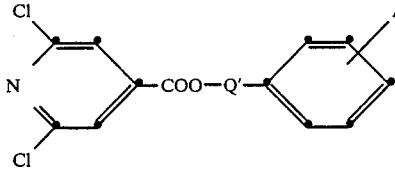

| No. | Q' | A' | physical data |
|---|---|---|---|
| 1.67 | —CH(CH₃)— | 4-CH₃ | |
| 1.68 | —CH(CH(CH₃)C₂H₅)— | H | |
| 1.69 | —CH(CH₃)— | 2-NO₂ | |
| 1.70 | —CH(CH₃)— | 3-NO₂ | |
| 1.71 | —CH(CH₃)— | 4-NO₂ | |
| 1.72 | —CH(CCl₃)— | H | |
| 1.73 | —CH(CF₃)— | H | $n_D^{30}$ 1,5259 |
| 1.74 | —CH(CH₃)— | 2-CF₃ | |
| 1.75 | —CH(CH₃)— | 4-CF₃ | |
| 1.76 | —CH(CH₃)— | 2,3,4-trimethoxy | |
| 1.77 | —CH(CH₃)— | 3,4,5-trimethoxy | |
| 1.78 | —CH₂— | 2,6-di-Cl | |
| 1.79 | —CH₂— | 2,4-di-Cl | |
| 1.80 | —C(CH₃)₂— | 4-C₆H₅ | |
| 1.81 | —CH[CO-(2,4-di-Cl-phenyl)] | 2,4-di-Cl | |
| 1.82 | —CH[CO-(4-OMe-phenyl)] | 4-OCH₃ | |
| 1.83 | 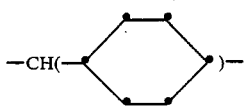 | H | |
| 1.84 | —C(CH₃)₂CH₂— | H | m.p. 86–88° C. |
| 1.85 | —CH₂— | 2,3-di-Cl | m.p. 78–80° C. |
| 1.86 | —CH₂CH(n-C₃H₇)— | 2,4-di-Cl | m.p. 91–93° C. |
| 1.87 | —CH(CH₃)— | 2-CH₃-4-(O—⬡—Cl) | m.p. 79–81° C. |
| 1.88 | —CH(CN)— | H | $n_D^{30}$ 1,5673 |
| 1.89 | —CH(CH₃)CH₂— | 2-OCH₃ | $n_D^{30}$ 1,5563 |
| 1.90 | —CH(CH₃)— | 2-OCHF₂-4-F-5-NO₂ | $n_D^{30}$ 1,5493 |

TABLE 2

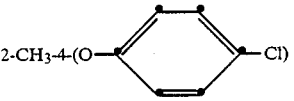

| No. | Q' | Hal | A' | physical Data |
|---|---|---|---|---|
| 2.1 | —CH₂— | Br | H | m.p. 89–91° C. |
| 2.2 | —CH₂— | F | H | |
| 2.3 | —CH₂— | J | H | |
| 2.4 | —CH(CH₃)— | Br | 2,4-di-Cl | |
| 2.5 | —CH(C₂H₅)— | Br | 2,4-di-Cl | |
| 2.6 | —CH(CH₃)— | J | H | |
| 2.7 | —CH—(4-chlorophenyl)- | Br | 3,4-di-OCH₃ | |
| 2.8 | —CH₂— | | 4-Me | |
| 2.9 | —CH(C₆H₅)— | Br | H | |
| 2.10 | —CH(C₆H₅)— | J | H | |
| 2.11 | —C(C₆H₅)₂— | Br | H | |
| 2.12 | —CH₂— | Br | 4-C₆H₅ | |
| 2.13 | —CH₂— | Br | 4-OC₆H₅ | |
| 2.14 | —CH₂— | F | 3-NO₂ | |
| 2.15 | —CH₂—CH₂ | Br | H | |
| 2.16 | —CH₂—CH₂—CH₂— | Br | H | |
| 2.17 | —CH₂—CH₂— | J | H | |

TABLE 2-continued

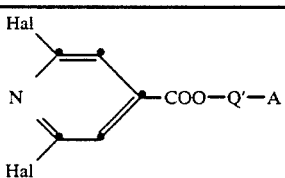

| No. | Q' | Hal | A' | physical Data |
|---|---|---|---|---|
| 2.18 | —CH(—△—)— | Br | 2,4-di-Cl | |
| 2.19 | —CH(COOCH$_3$)— | Br | 2,4-di-Cl | |
| 2.20 | —CH(C$_6$H$_5$)— | Br | 4-Cl | |
| 2.21 | —C(CH$_3$)$_2$— | Br | H | |
| 2.22 | —CH(—⌬H—)— | Br | H | |
| 2.23 | —CH(CO-phenyl)- | Br | H | |
| 2.24 | —CH$_2$— | Br | 4-Cl | m.p. 91–92° C. |

TABLE 3

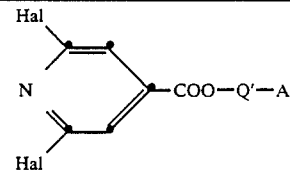

| No. | Q' | Hal | A | physical data |
|---|---|---|---|---|
| 3.1 | —CH$_2$— | Cl | A$_2$ | m.p. 84–86° C. |
| 3.2 | —CH$_2$— | Cl | A$_3$ | m.p. 86–90° C. |
| 3.3 | —CH$_2$— | Cl | A$_4$ | m.p. 39–41° C. |
| 3.4 | —CH$_2$— | Cl | A$_5$ | m.p. 42–43° C. |
| 3.5 | —CH$_2$— | Cl | A$_6$ | m.p. 53–54° C. |
| 3.6 | —CH$_2$— | Cl | A$_7$ | m.p. 58–59° C. |
| 3.7 | —CH$_2$— | Cl | A$_8$ | m.p. 62–64° C. |
| 3.8 | —CH$_2$— | Cl | A$_9$ | m.p. 78–80° C. |
| 3.9 | —CH$_2$— | Cl | A$_{10}$ | m.p. 81–84° C. |
| 3.10 | —CH$_2$— | Br | A$_2$ | |
| 3.11 | —CH$_2$— | Br | A$_3$ | |
| 3.12 | —CH$_2$— | Br | A$_4$ | |
| 3.13 | —CH$_2$— | Br | A$_5$ | |
| 3.14 | —CH$_2$— | Br | A$_6$ | |
| 3.15 | —CH$_2$— | Br | A$_9$ | |
| 3.16 | —CH$_2$— | Br | A$_{10}$ | |
| 3.17 | —CH$_2$— | F | A$_2$ | |
| 3.18 | —CH$_2$— | F | A$_3$ | |
| 3.19 | —CH$_2$— | J | A$_4$ | |
| 3.20 | —CH$_2$— | F | A$_6$ | |
| 3.21 | —CH$_2$— | F | A$_9$ | |
| 3.22 | —CH$_2$—CH$_2$— | Cl | A$_2$ | |
| 3.23 | —CH$_2$—CH$_2$— | Cl | A$_9$ | |
| 3.24 | —CH$_2$—CH$_2$—CH$_2$— | Cl | A$_3$ | |
| 3.25 | —CH—(CH$_3$)— | Cl | A$_8$ | |
| 3.26 | —CH(COOCH$_3$)— | Cl | A$_6$ | |
| 3.27 | —CH(COOC$_2$H$_5$)— | Cl | A$_7$ | |
| 3.28 | —CH(COOCH$_3$)— | Cl | A$_9$ | |
| 3.29 | —CH(COO(C$_3$H$_7$)i)— | Br | A$_{10}$ | |
| 3.30 | —CH$_2$—CH$_2$— | Br | A$_6$ | |

TABLE 3-continued

| No. | Q' | Hal | A | physical data |
|---|---|---|---|---|
| 3.31 | —CH$_2$—CH$_2$—CH$_2$— | J | A$_9$ | |
| 3.32 | —C(CH$_3$)$_2$— | Cl | A$_3$ | |
| 3.33 | —C(CH$_3$)$_2$— | Cl | A$_4$ | |
| 3.34 | —C(CH$_3$)$_2$— | Cl | A$_9$ | |
| 3.35 | —C(CH$_3$)$_2$— | Cl | A$_9$ | |
| 3.36 | —C(CH$_3$)$_2$— | Cl | A$_{10}$ | |
| 3.37 | —C(CH$_3$)$_2$— | Br | A$_7$ | |
| 3.38 | —CH(CH$_3$)— | Cl | A$_2$ | |
| 3.39 | —CH(C$_6$H$_5$)— | Cl | A$_8$ | |
| 3.40 | —CH(C$_2$H$_5$)— | Cl | A$_9$ | |
| 3.41 | —CH$_2$(C(CH$_3$)$_2$)— | Cl | A$_{10}$ | |
| 3.42 | —CH(2,4-di-Cl—C$_6$H$_3$)— | Br | A$_4$ | |
| 3.43 | —CH(2,4-di-Cl—C$_6$H$_3$)— | Cl | A$_7$ | |
| 3.44 | —CH(2,4-di-Cl—C$_6$H$_3$)— | Cl | A$_8$ | |
| 3.45 | —CH$_2$—CH$_2$—CH$_2$— | Cl | A$_9$ | |
| 3.46 | —CH$_2$—CH(CH$_3$)— | Cl | A$_9$ | |
| 3.47 | —CH$_2$CH(CH$_3$)—[A] | Cl | A$_{10}$ | |
| 3.48 | —CH$_2$—CH(C$_2$H$_5$)—[A] | Cl | A$_9$ | |
| 3.49 | —CH$_2$—CH(C$_3$H$_7$i)—[A] | Cl | A$_9$ | |
| 3.50 | —CH$_2$—C(C$_2$H$_5$)$_2$—[A] | Cl | A$_9$ | |
| 3.51 | —CH$_2$—CH(C$_4$H$_9$-n)—[A] | Cl | A$_9$ | |
| 3.52 | —CH[CO—(2,4-di-Cl-phenyl)] | Cl | A$_7$ | |

TABLE 4

Hal—pyridyl—COS—Q—A (with Hal substituents)

| No. | Q | Hal | A | physical data |
|---|---|---|---|---|
| 4.01 | —CH$_2$— | Cl | phenyl | m.p. |

TABLE 4-continued $$\underset{\text{Hal}}{\overset{\text{Hal}}{N}}\!\!\diagdown\!\!=\!\!\diagup\!\!\text{COS}-\text{Q}-\text{A}$$

| No. | Q | Hal | A | physical data |
|---|---|---|---|---|
| | | | | 63–65° C. |
| 4.02 | —CH$_2$— | Br | phenyl | |
| 4.03 | —CH$_2$— | Cl | 4-Cl—C$_6$H$_4$— | |
| 4.04 | —CH$_2$— | Cl | 2,4-DiCl—C$_6$H$_3$— | |
| 4.05 | —CH—CH$_3$— | Cl | 2,4-DiCl—C$_6$H$_3$— | |
| 4.06 | —CH(COOCH$_3$)— | Br | 2,4-DiCl—C$_6$H$_3$— | |
| 4.07 | —CH$_2$— | F | phenyl | |
| 4.08 | —CH$_2$CH$_2$— | Cl | phenyl | |
| 4.09 | —CH$_2$CH$_2$CH$_2$— | Cl | phenyl | |
| 4.10 | —CH(△)— | Cl | phenyl | |
| 4.11 | —CH$_2$— | Cl | A$_2$ | |
| 4.12 | —CH$_2$— | Br | A$_4$ | |
| 4.13 | —CH$_2$— | Cl | A$_6$ | |
| 4.14 | —CH$_2$— | J | A$_7$ | |
| 4.15 | —CH$_2$— | Cl | A$_8$ | |
| 4.16 | —CH(CH$_3$)— | Cl | 2,4-di-Cl—C$_6$H$_3$— | |
| 4.17 | —CH$_2$— | Cl | C$_6$H$_5$—C$_6$H$_4$— | |
| 4.18 | —CH—(CH$_3$)— | Cl | diphenyl(1',4')— | |
| 4.19 | —CH$_2$— | Cl | A$_4$ | m.p. 88–90° C. |

2. FORMULATION EXAMPLES FOR LIQUID ACTIVE INGREDIENTS OF FORMULA I (THROUGHOUT, PERCENTAGES ARE BY WEIGHT)

| 2.1 Emulsifiable concentrates | (a) | (b) | (c) |
|---|---|---|---|
| a compound from the Tables | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | (a) | (b) | (c) | (d) |
|---|---|---|---|---|
| a compound from the Tables | 80% | 10% | 5% | 95% |
| ethylene glycol monomethyl ether | 20% | — | — | — |
| polyethylene glycol MW 400 | — | 70% | — | — |
| N-methyl-2-pyrrolidone | — | 20% | — | — |
| epoxidised coconut oil | — | — | 1% | 5% |
| petroleum factor (boiling range 160–190° C.) | — | — | 94% | — |

(MW = molecular weight)

These solutions are suitable for application in the form of micro-drops.

| 2.3. Granulates | (a) | (b) |
|---|---|---|
| a compound from the Tables | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound from the Tables | 2% | 5% |
| highly dispersed silicic acid | 1% | 5% |
| talcum | 97% | — |
| kaolin | — | 90% |

Ready-for-use dusts are obtained by homogeneously mixing the carriers with the active ingredient.

Formulation Examples for solid active ingredients of formula I (throughout, percentages are by weight)

| 2.5. Wettable powders | (a) | (b) | (c) |
|---|---|---|---|
| a compound from the Tables | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is homogeneously ground in a suitable mill, affording wettable powders which can be diluted with water to give suspensions of the desired concentration.

| 2.6. Emulsifiable concentrate | |
|---|---|
| a compound from the Tables | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound from the Tables | 5% | 8% |
| talcum | 95% | — |
| kaolin | — | 92% |

Ready-for-use dusts are obtained by mixing the active ingredient with the carriers and grinding the mixture in a suitable mill.

| 2.8. Extruder granulate | |
|---|---|
| a compound from the Tables | 10% |
| sodium lignosulfonate | 2% |
| carboxymethylcellulose | 1% |

-continued

| 2.8. Extruder granulate | |
|---|---|
| kaolin | 87% |

The active ingredient is mixed and ground with the adjuvants, and the mixture is moistened with water. The mixture is extruded and then dried in a stream of air.

| 2.9. Coated granulate | |
|---|---|
| a compound from the Tables | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound from the Tables | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a aqueous emulsion | 75% 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

EXAMPLE 3.1

Protection against Colletotrichum lagenarium on *Cucumis sativus L.*

(a) After 2 weeks' cultivation, cucumber plants are sprayed with a spray mixture prepared from a wettable powder formulation of the test compound (concentration: 20 ppm).

After 3 weeks the plants are infected with a spore suspension (1.5×105 spores/ml) of the fungus and incubated for 36 hours at high humidity and a temperature of 23° C. Incubation is then continued at normal humidity and at from 22° to 23° C.

The protective action is assessed on the basis of the fungal attack 7 to 8 days after infection.

Fungal attack on untreated and infected control plants in the test was 100%.

Compounds from Tables 1 to 4 exhibited good protection against *Colletotrichum lagenarium*. For example plants that had been treated, for example, with compounds 1.1, 1.5, 1.6, 1.7, 1.8, 1.13, 1.17, 1.26, 1.37, 1.41, 1.54, 1.62, 1.66, 1.73, 1.84, 1.87, 1.88, 1.89, 2.1 and 2.24 remained almost completely free of Colletotrichum (attack 10 to 0%).

(b) Cucumber seed are dressed with a solution of the test compound (concentration: 180 g/100 kg of seed). The seeds are sown. After 4 weeks the plants are infected with a spore suspension (1.5×105 spores/ml) of the fungus and incubated for 36 hours at high humidity and a temperature of 23° C. Incubation was then continued at normal humidity and at 22° to 23° C. The protective action is assessed on the basis of the fungal attack 7 to 8 days after infection.

In this test, fungal attack was 100% in the case of infected control plants of which the seeds had not been treated.

EXAMPLE 3.2

Action against *Xanthomonas oryzae* on rice (*Oryza sativa*)

(a) After 3 weeks' cultivation in a greenhouse, rice plants of the variety "Calora" or "S6" are sprayed with the test substance in the form of a spray mixture (0.02% active ingredient). After this spray coating has dried for 1 day the plants are placed in a climatic chamber at 24° C. and 75–85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The residual activity of the test substance is evaluated on the basis of the extent of these disease symptoms.

(b) After a cultivation period of 3 weeks in a greenhouse, rice plants of the variety "Calora" or "S6" are watered with a suspension of the test substance (0.006% active ingredient based on the volume of soil). Three days after this treatment the plants are placed in a climatic chamber at 24° C. and 75–85% relative humidity and infected. The infection is carried out by cutting off the leaf tips with shears that have beforehand been immersed in a suspension of *Xanthomonas oryzae*. After an incubation period of 10 days the cut leaves that have been attacked become shrivelled, roll up and become necrotic. The systemic activity of the test substance is evaluated on the basis of the extent of these disease symptoms.

Compounds from Tables 1 to 4 exhibited a good protective action against *Xanthomonas oryzae*. For example in test (a) compounds 1.7, 1.8 and 3.8 and in test (b) compounds 1.6 and 1.8 confined the bacterial attack to 0 to 20%. On the other hand, disease attack was 100% on untreated and infected control plants.

EXAMPLE 3.3

Action against *Xanthomonas vesicatoria* on paprika (*Capsicum annuum*)

(a) After 3 weeks' cultivation in a greenhouse, paprika plants of the variety "California Wonder" are sprayed with the test substance in the form of a spray mixture (0.02% active ingredient). After the spray coating has dried for one day, the plants are placed in a climatic chamber at 26° C. and 95–100% relative humidity and infected by spraying the undersides of the leaves with a standardised suspension of *Xanthomonas vesicatoria*. After an incubation period of 6 days, round, initially watery, later necrotic, light specks form on the leaves attacked. The residual activity of the test substance is evaluated on the basis of the extent of these flecks.

(b) After a cultivation period of 3 weeks in a greenhouse, paprika plants of the variety "California Wonder" are watered with a suspension of the test substance (0.006% active ingredient based on the volume of soil). Three days after this treatment the plants are placed in a climatic chamber at 26° C. and 95–100% relative humidity and infected by spraying the undersides of the leaves with a standardised suspension of *Xanthomonas vesicatoria*. After an incubation period of 6 days, round, initially watery, later necrotic, light specks form on the leaves attacked. The systemic activity of the test substance is evaluated on the basis of the extent of these flecks.

Compounds from Tables 1 to 4 exhibited a good protective action against *Xanthomonas vesicatoria*. For example in test (a) compounds 1.7, 1.8, 3.8 and in test (b) compounds 1.7 and 3.8 confined the bacterial attack to 0 to 20%. On the other hand, disease attack was 100% on untreated and infected control plants.

EXAMPLE 3.4

Action against *Pseudomonas lachrymans* on *Cucumis sativus L.*

After 2 weeks' cultivation, cucumber plants are sprayed with a spray mixture prepared from a wettable powder formulation of the test compound (concentration: 20 ppm).

After 1 week, the plants are infected with a bacterial suspension (108 bacteria/ml) and incubated for 7 days at high humidity and a temperature of 23° C.

The protective action is evaluated 7 to 8 days after infection on the basis of the bacterial attack.

Disease attack was 100% on untreated and infected control plants in the test.

Compounds from Tables 1 to 4 exhibited a good protective action against *Pseudomonas lachrymans*. For example, plants treated, for example, with compound No. 1.7 or 3.8 remained almost completely free of Pseudomonas (10 to 0% attack).

EXAMPLE 3.5

Action against *Phytophthora infestans* on tomato plants (a) After 3 weeks' cultivation, tomato plants are sprayed with a spray mixture (0.02% active ingredient) prepared as described above from a wettable powder formulation of the test compound. After 24 hours the treated plants are infected with a sporangia suspension of the fungus. The fungal attack was evaluated after incubating the infected plants for 5 days at 90–100% relative humidity and 20° C.

(b) After a cultivation period of 3 weeks tomato plants were watered with a spray mixture (0.002% active ingredient based on the volume of soil) prepared as described above from a wettable powder formulation of the test compound. Care was taken that the spray mixture did not come into contact with the parts of the plant above the soil. 48 hours later the treated plants were infected with a sporangia suspension of the fungus. The fungal attack is evaluated after incubating the infected plants for 5 days at 90–100% relative humidity and 20° C.

Compounds from Tables 1 to 4 exhibited a good protective action against Phytophthora. For example, in examples (a) and (b) the application of compound 1.07, 1.13, 1.17, 1.26, 1.37, 1.54, 1.62, 1.66, 1.87, 1.88, 1.89, 1.90, 2.1, 2.4 or 3.8 confined attack to 0 to 20%. 100% of the untreated and infected control plants had withered.

EXAMPLE 3.6

Action against *Peronospora tabacina* on tobacco (a) Tobacco plants (8 weeks old) are sprayed with a formulated solution of the active ingredient (concentration: 200 ppm). Four days after the treatment, the plants are inoculated with a sporangia suspension of *Peronospora tabacina* (104 spores/ml), kept for 20 hours at 25° C. and high humidity in the dark, and then further incubated with normal day/night alternation.

(b) Tobacco plants (8 weeks old) are treated with a formulated solution of the active ingredient (concentration: 6 ppm) by soil application. Four days later, the plants are inoculated with a sporangia suspension of *Peronospora tabacina* (104 spores/ml), kept for 20 hours at 25° C. and high humidity in the dark, and then further incubated with normal day/night alternation.

The symptoms in tests (a) and (b) are evaluated on the basis of the leaf surface attacked by fungi.

Compounds from Tables 1 to 4 exhibited a good protective action against *Peronospora tabacina*.

Attack on untreated and infected plants was 80 to 100%.

EXAMPLE 3.7

Action against *Erysiphe graminis* on barley (a) Barley plants about 8 cm in height were sprayed with a spray mixture (0.02% active ingredient) prepared from a wettable powder formulation of the test compound. 3 to 4 hours later, the treated plants were dusted with conidia of the fungus. The infected barley plants were stood in a greenhouse at about 22° C. and the fungal attack was evaluated after 10 days.

(b) Barley plants about 8 cm in height were watered with a spray mixture (0.006% active ingredient, based on the volume of soil) prepared from a wettable powder formulation of the test compound. Care was taken that the spray mixture did not come into contact with the parts of the plants above the soil. The treated plants were infected 48 hours later with conidia of the fungus. The infected barley plants were stood in a greenhouse at about 22° C. and evaluation of fungal attack was made after 10 days.

Compounds from Tables 1 to 4, for example compounds 1.07 and 3.8, confined fungal attack to less than 20%, whilst attack on untreated and infected control plants was 100%.

EXAMPLE 3.8

Action against *Pyricularia oryzae* on rice plants (a) After 2 weeks' cultivation, rice plants are sprayed with a spray mixture (0.002% active ingredient) prepared from a wettable powder formulation of the test compound. After 48 hours, the treated plants are infected with a conidia suspension of the fungus. Evaluation of fungal attack is made after incubation for 5 days at 95–100% relative humidity and 24° C.

(b) 2 week-old rice plants that are planted in pots are watered with a spray mixture (0.006% active ingredient based on the volume of soil) prepared from a wettable powder formulation of the test compound. The pots are then filled with water until the lowest parts of the stalks of the rice plants stand in water. After 96 hours the treated rice plants are infected with a conidia suspension of the fungus. Evaluation of fungal attack is made after incubation of the infected plants for 5 days at 95–100% relative humidity and approximately 24° C.

Rice plants that had been treated with a spray mixture containing one of the compounds from Tables 1 to 4 as active ingredient exhibited only slight fungal attack compared with untreated control plants (100% attack). For example in test (a) compounds 1.5, 1.7, 1.41 and 1.84 and in test (b) compounds 1.1, 1.5, 1.7, 1.8, 1.26, 1.37, 1.85, 1.86, 1.90 and 2.1 confined fungal attack to 5 to 20%.

EXAMPLE 3.9

Action against *Pseudomonas tomato* on tomato plants (a) After 3 weeks' cultivation, tomato plants are treated by foliar application with a spray mixture prepared from a wettable powder formulation of the test compound (concentration: 200 ppm). 3.5 weeks later the plants are inoculated with a bacterial suspension (108 bacteria/ml) and incubated for 6 days at high humidity and at a temperature of 25° C. The protective action is evaluated 7 to 8 days after inoculation on the basis of the bacterial attack.

Attack was 100% on untreated and infected control plants in this test.

Compounds from Tables 1 to 4 exhibited a good protective action against *Pseudomonas tomato*. For example plants that had been treated, for example, with compounds 1.7, 1.8 and 3.8, remained substantially free of Pseudomonas (attack: 20 to 0%).

(b) After 3 weeks' cultivation tomato plants are treated by soil application with a spray mixture prepared from a wettable powder formulation of the test compound (concentration: 60 ppm based on the volume of soil). After 3.5 weeks the plants are inoculated with a bacterial suspension (108 bacteria/ml) and incubated for 6 days at high humidity and at a temperature of 25° C.

The protective action is evaluated 7 to 8 days after inoculation on the basis of the bacterial attack.

Attack was 100% on untreated and infected control plants in this test.

Compounds from Tables 1 to 4 exhibited a good protective action against *Pseudomonas tomato*. For example plants that had been treated, for example, with compound 1.7, 1.8 or 3.8 remained almost completely free of Pseudomonas (attack: 20 to 0%).

EXAMPLE 3.10

Action against Tobacco Mosaic Virus on tobacco

Tobacco plants (8 weeks old) are injected with a formulated solution of the test compound (concentration: 200 ppm). After 4 days the plants are mechanically inoculated with a suspension of Tobacco Mosaic Virus (0.5 μg/ml+carborundum) and incubated at a temperature of 20°-22° C.

The protective action is evaluated 7 days after inoculation on the basis of the number and size of the local lesions.

Plants that had been treated with the compounds from Tables 1 to 4 exhibited a marked reduction in lesions compared with untreated and infected control plants on which there was 100% attack.

What is claimed is:

1. A compound of formula I

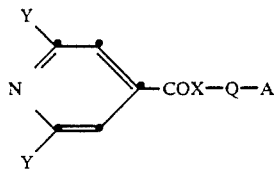

in which
Y is halogen;
X is oxygen or sulfur;
Q is $C_1$-$C_3$alkylene, propenylene, $C_1$-$C_3$alkylene mono- or di-substituted by R, or propenylene mono- or di-substituted by R;
R is $C_1$-$C_4$alkyl, $C_1$-$C_4$haloalkyl having from 1 to 3 halogen atoms, cyano, $C_2$-$C_5$alkoxycarbonyl, $C_3$-$C_6$cycloalkyl, phenyl, or phenyl substituted by $C_1$-$C_4$alkyl, $C_1$-$C_4$alkoxy, halogen, trifluoromethyl, trichloromethyl, nitro or by cyano, or benzoyl or benzoyl substituted by $C_1$-$C_4$alkyl, $C_1$-$C_4$alkoxy, trifluoromethyl, trichloromethyl, nitro or by cyano;
A is phenyl, biphenyl, phenoxyphenyl, naphthyl, pyridyl, furyl, thienyl, imidazolyl or triazolyl, each of these radicals being unsubstituted or substituted by halogen, $C_1$-$C_4$alkyl, $C_1$-$C_3$alkoxy, $C_1$-$C_3$haloalkoxy having from 1 to 3 halogen atoms, trifluoromethyl, nitro or by cyano; with the proviso (1) that if A is imidazolyl or triazolyl R may not be phenyl or benzoyl, and (2) that A and the R substituent in Q may together contain no more than 3 rings.

2. A compound of formula I

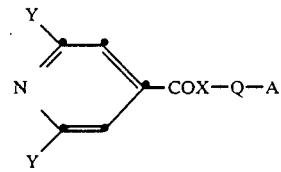

in which
Y is halogen;
X is oxygen or sulfur;
Q is $C_1$-$C_3$alkylene, propenylene, $C_1$-$C_3$alkylene mono- or di-substituted by R, or propenylene mono- or di-substituted by R;
R is $C_1$-$C_4$alkyl, $C_1$-$C_4$haloalkyl having from 1 to 3 halogen atoms, cyano, $C_2$-$C_5$alkoxycarbonyl, $C_3$-$C_6$cycloalkyl, phenyl, or phenyl substituted by $C_1$-$C_4$alkyl, $C_1$-$C_4$alkoxy, trifluoromethyl, trichloromethyl, nitro or by cyano, or benzoyl or benzoyl substituted by $C_1$-$C_4$alkyl, $C_1$-$C_4$alkoxy, trifluoromethyl, trichloromethyl, nitro or by cyano;
A is phenyl, biphenyl, phenoxyphenyl, naphthyl, pyridyl, furyl, thienyl, imidazolyl or triazolyl, each of these radicals being unsubstituted or substituted by halogen, $C_1$-$C_4$alkyl, $C_1$-$C_3$alkoxy, trifluoromethyl, nitro or by cyano; with the proviso (1) that if A is imidazolyl or triazolyl R may not be phenyl or benzoyl, and (2) that A and the R substituent in Q may together contain no more than 3 rings.

3. A compound according to claim 2 in which
Y is simultaneously chlorine or bromine;
X is oxygen;
Q is methylene or methylene substituted by R;
R is $C_1$-$C_3$alkyl, phenyl or phenyl substituted by halogen or by methoxy;
A is phenyl, phenyl substituted by halogen, or pyridyl, furyl, thienyl, imidazolyl or triazolyl.

4. A compound according to claim 2 in which
Y is chlorine;
X is oxygen;
Q is methylene substituted by R;
R is methyl, ethyl, phenyl or 2,4-dichlorophenyl;
A is phenyl substituted by chlorine and/or by fluorine, especially 2,4-dichlorophenyl.

5. A compound from the group:

2,6-dichloroisonicotinic acid benzyl ester;
2,6-dichloroisonicotinic acid α-methylbenzyl ester;
2,6-dichloroisonicotinic acid α-ethylbenzyl ester;
2,6-dichloroisonicotinic acid α-phenylbenzyl ester;
2,6-dichloroisonicotinic acid α-(4-chlorophenyl)-benzyl ester.

6. A composition for protecting plants against attack by microorganisms that contains an effective amount of at least one compound according to claim 1 as active component together with customary carriers and adjuvants.

7. A method of protecting plants against attack by phytopathogenic microorganisms which comprises applying as active ingredient to the plant or to the locus thereof an effective amount of a compound according to claim 1.

8. A composition of claim 6 that contains, as active component, at least one compound selected from the group consisting of
2,6-dichloroisonicotinic acid benzyl ester;
2,6-dichloroisonicotinic acid α-methylbenzyl ester;
2,6-dichloroisonicotinic acid α-ethylbenzyl ester;
2,6-dichloroisonicotinic acid α-phenylbenzyl ester;
2,6-dichloroisonicotinic acid α-(4-chlorophenyl)-benzyl ester.

* * * * *